United States Patent
Bouiller et al.

(10) Patent No.: US 7,479,717 B2
(45) Date of Patent: Jan. 20, 2009

(54) TURBOMACHINE HAVING A DEVICE FOR AUTOMATICALLY DETECTING FERROMAGNETIC PARTICLES IN AN OIL ENCLOSURE

(75) Inventors: Philippe Bouiller, Samoreau (FR); Stephane Rousselin, Hericy (FR)

(73) Assignee: Snecma, Paris (FR)

( * ) Notice: Subject to any disclaimer, the term of this patent is extended or adjusted under 35 U.S.C. 154(b) by 478 days.

(21) Appl. No.: 11/270,724

(22) Filed: Nov. 10, 2005

(65) Prior Publication Data

US 2006/0138888 A1    Jun. 29, 2006

(30) Foreign Application Priority Data

Nov. 16, 2004  (FR) .................................. 04 12115

(51) Int. Cl.
  *H02K 5/16* (2006.01)
  *F16C 41/04* (2006.01)
(52) U.S. Cl. ........................ 310/68 B; 310/90; 384/448
(58) Field of Classification Search ............. 310/90, 310/68 B; 73/116; 384/448; 290/52
  See application file for complete search history.

(56) References Cited

U.S. PATENT DOCUMENTS 5,264,832 A    11/1993  Parmer ..................... 340/631
5,376,827 A *  12/1994  Hines ......................... 290/52
5,614,830 A    3/1997   Dickert et al. ............... 324/553
5,696,331 A    12/1997  Otsuka et al. ............... 73/865.8

FOREIGN PATENT DOCUMENTS

EP    1 164 022 A2    12/2001
WO   WO 01/36966 A2   5/2001

* cited by examiner

Primary Examiner—Karl Tamai
Assistant Examiner—David W. Scheuermann
(74) Attorney, Agent, or Firm—Oblon, Spivak, McClelland, Maier & Neustadt, P.C.

(57) ABSTRACT

A turbomachine having a longitudinal axis, the turbomachine comprising an annular rotor centered on the longitudinal axis of the turbomachine, an annular stator disposed coaxially around the rotor, at least one ball bearing disposed on the rotor and rotatably supporting said stator, the inside of the rotor defining part of an oil enclosure for cooling and lubricating the balls of the bearing, an electricity generator having a secondary magnetic circuit secured to the stator and a primary magnetic circuit constrained to rotate with the rotor, and a detector device for automatically detecting ferromagnetic particles in the oil enclosure, said detector device being powered electrically by electromagnetic induction.

9 Claims, 2 Drawing Sheets

TURBOMACHINE HAVING A DEVICE FOR AUTOMATICALLY DETECTING FERROMAGNETIC PARTICLES IN AN OIL ENCLOSURE

BACKGROUND OF THE INVENTION

The present invention relates to the general field of turbomachines provided with devices for automatically detecting ferromagnetic particles in an oil enclosure.

The invention relates more particularly to an aeroengine in which the electricity generator is formed by a secondary magnetic circuit secured to one of its stators and a primary magnetic circuit constrained to rotate with one of its rotors.

In the field of aeroengines, ancillaries (e.g. actuators) are generally mostly hydraulic. For reasons of reliability, safety, and compactness, it is becoming more and more common for such hydraulic ancillaries to be replaced by electrical ancillaries.

For this purpose, it has become necessary to include an electricity generator in a turbomachine having electrical ancillaries. Such a generator serves simultaneously to feed electricity to the various items of electrical equipment belonging to the turbomachine (pumps, actuators, etc.), and also to start the turbomachine.

In order to take advantage of the arms (or spacers) that hold the turbomachine casing, for the purpose of passing electric cables, the solution that is generally selected is to install such an electricity generator in one of the oil enclosures of the high pressure body of the turbomachine. Such an oil enclosure is used to cool and lubricate the ball bearings between the various shafts. Typically, the electricity generator comprises a coil (forming a secondary magnetic circuit) and magnets (forming a primary magnetic circuit) that are secured respectively to the stator and to the rotor of the high-pressure turbine of the turbomachine.

In addition, it is also known to fit the oil enclosures of turbomachines with detectors for detecting wear of the ball bearings between the shafts and associated with said enclosures. Such sensors are generally in the form of external magnetic plugs. These plugs comprise magnets that capture the ferromagnetic particles inside the oil enclosure that stem from ball bearing wear. During ground maintenance operations on the turbomachine, the magnetic plugs are dismantled from the turbomachine and spectrographic analysis is used to determine the origins and the quantities of the particles that have been collected in order to deduce therefrom the wear state of the ball bearings.

When the turbomachine is fitted with an electricity generator as described above, the problem arises of how to detect ball bearing wear. The presence of magnets constituting the primary magnetic circuit of the electricity generator inside the oil enclosure has the consequence of falsifying bearing wear detection by means of magnetic plugs.

More generally, detecting ball bearing wear by means of magnetic plugs turns out to be an operation that is time consuming and incomplete. In addition to the fact that spectrographic analysis is necessary, the magnetic plugs can be read only on specific occasions (only while the turbomachine is being subjected to maintenance on the ground). As a result the level of ball bearing wear is sometimes detected only late, and that can compromise turbomachine safety.

OBJECT AND SUMMARY OF THE INVENTION

A main object of the present invention is thus to mitigate such drawbacks by proposing a turbomachine in which ball bearing wear detection is not compromised by the presence of an electricity generator.

To this end, there is provided a turbomachine comprising an annular rotor centered on the longitudinal axis of the turbomachine, an annular stator disposed coaxially around the rotor, at least one ball bearing disposed on the rotor and rotatably supporting said stator, the inside of the rotor defining part of an oil enclosure for cooling and lubricating the balls of the bearing, and an electricity generator having a secondary magnetic circuit secured to the stator and a primary magnetic circuit constrained to rotate with the rotor, the turbomachine further including a detector device for automatically detecting ferromagnetic particles in the oil enclosure, said detector device being powered electrically by electromagnetic induction.

According to a particular characteristic of the invention, the detector device comprises: a pair of electrodes disposed on the inside annular face of the rotor, each electrode comprising a metal film and a plurality of substantially parallel metal tracks, the tracks of each of the electrodes being interleaved with between the tracks of the other electrode; a secondary magnetic circuit secured to the rotor which is excited by the magnetic field created by the secondary magnetic circuit of the electricity generator of the turbomachine so as to apply a voltage between the electrodes such that when ferromagnetic particles are received between the tracks of the electrodes, an electrical signal is generated between said electrodes; and a detector for detecting the intensity of the electrical signal generated between the electrodes, the intensity of said electrical signal being a function of the ferromagnetic particles present in the oil enclosure.

As a result, the presence of the primary magnetic circuit of the electricity generator is used to attract magnetically the ferromagnetic particles that are generated by ball bearing wear onto the magnetic tracks of the detector device. This enables accurate detection of ball bearing wear to be obtained.

Furthermore, such a ball bearing wear detector device presents the advantage of being powered independently since it is fed with electricity merely by electromagnetic induction. The secondary magnetic circuit of the detector device can thus be constituted merely by a coil of conductor wire.

According to another particular characteristic of the invention, the detector device further includes a radio transmitter connected to the detector in order to transmit a radio signal to a full authority digital engine controller (FADEC) of the turbomachine, which signal is a function of the density of ferromagnetic particles present in the oil enclosure.

The radio transmitter transmits the signal that is a function of the density of ferromagnetic particles present in the oil enclosure continuously and in real time to the FADEC. Thus, the FADEC is continuously informed about the real level of ball bearing wear. No inspection operation is then needed on the ground.

The metal film of each electrode of the detector device may extend substantially along the longitudinal axis of the turbomachine, and the metal tracks of each electrode may extend in a direction that is substantially transverse relative to said longitudinal axis of the turbomachine.

Alternatively, the metal tracks of each electrode of the detector device may extend substantially along the longitudinal axis of the turbomachine, and the metal film of each electrode may extend in a direction that is substantially transverse relative to said longitudinal axis of the turbomachine.

Preferably, the secondary magnetic circuit of the electricity generator is constituted by a coil wound on an inner annular face of the stator, and the primary magnetic circuit of the electricity generator is constituted by at least one magnet disposed on an outer annular face of the rotor.

The coil and the magnet(s) of the electricity generator are then advantageously isolated from the oil enclosure by annular sealing devices secured to the stator.

BRIEF DESCRIPTION OF THE DRAWINGS

Other characteristics and advantages of the present invention appear from the following description given with reference to the accompanying drawings which show an embodiment having no limiting character. In the figures.

DETAILED DESCRIPTION OF AN EMBODIMENT

Figure 1:
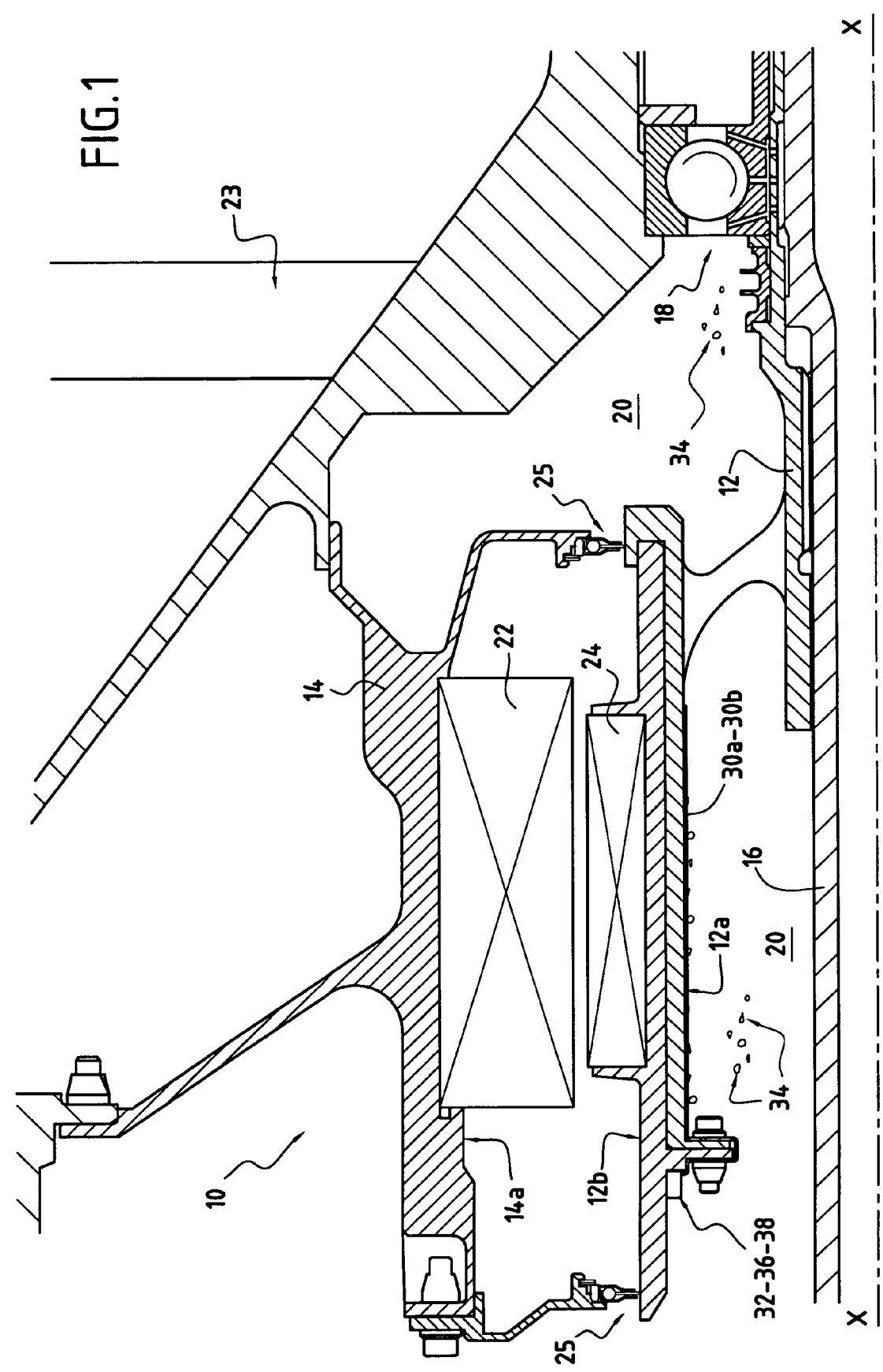
FIG. 1 is a fragmentary longitudinal section view of a turbomachine of the invention.

FIG. 1 is a fragmentary longitudinal section view of a turbomachine having a longitudinal axis X-X, and more precisely showing the high-pressure body 10 thereof. The turbomachine shown is an aeroengine.

The high-pressure body 10 of the turbomachine comprises in particular an annular rotor 12 centered on the longitudinal axis X-X, and an annular stator 14 disposed coaxially around the rotor 12. The rotor 12 is rotated by a shaft 16 of the low-pressure body of the turbomachine, which shaft is coaxial with the rotor. A ball bearing 18 is disposed on the rotor 12 in order to provide rotary support relative to the stator 14.

In conventional manner, an oil circulation circuit (not shown) serves to deliver oil to the ball bearing 18 in order to lubricate and cool the balls in the bearing. Oil that has lubricated and cooled the ball bearing 18 is then confined in an oil enclosure 20 that is defined radially in part by the rotor 12.

The turbomachine also has an electricity generator for feeding electricity to the various pieces of electrical equipment belonging to the turbomachine (pumps, actuators, etc.) and also to enable the turbomachine to be started.

The electricity generator operates on the basis of electromagnetic induction. It comprises a secondary magnetic circuit secured to the stator 14 and a primary magnetic circuit constrained to rotate with the rotor 12. By way of example, the secondary magnetic circuit may be constituted by a conductor wire coil 22 wound on the inside face 14a of the stator 14. The primary magnetic circuit may be formed by one or more magnets 24 mounted on the outside face 12b of the rotor 12.

When the turbomachine is in operation, rotation of the rotor 12 rotates the magnet(s) 24 of the electricity generator inside the coil 22 which remains stationary. This causes an induced current to appear in the conductor wire of the coil 22, which current is conveyed to various pieces of equipment in the turbomachine by electric cables (not shown) running along an arm (or spacer) 23 of the high-pressure body.

In FIG. 1, it can be seen that the coil 22 and the magnet(s) 24 of the electricity generator of the turbomachine are isolated from the oil enclosure 20 by annular sealing devices 25 of the lip gasket type that are secured to the stator 14.

Such a turbomachine further includes a device for automatically detecting ferromagnetic particles in the oil enclosure 20, the detector device being powered electrically by electromagnetic induction.

Figure 2:
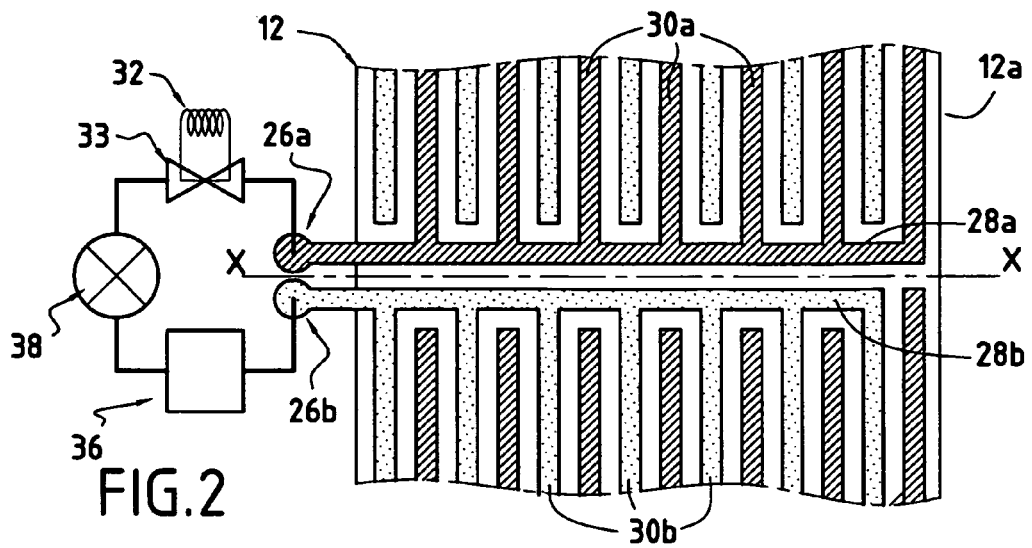
FIGS. 2 and 3 are diagrams showing two embodiments of the detector device of the FIG. 1 turbomachine.
Figure 3:
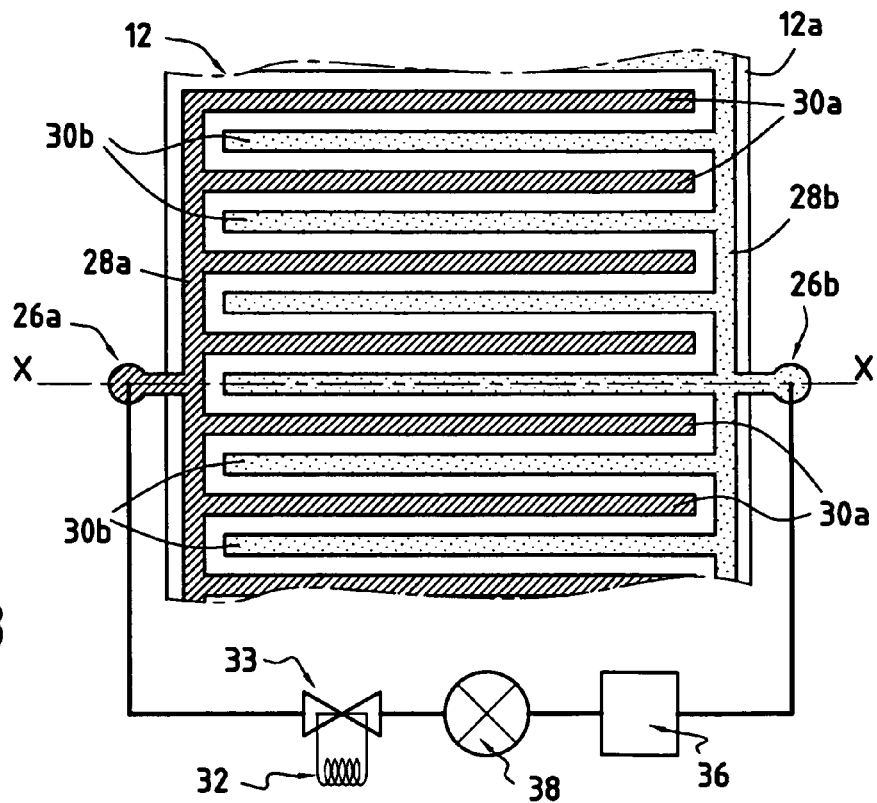

More precisely, and as shown in FIGS. 2 and 3, the detector device comprises a pair of electrodes 26a, 26b disposed on the annular inside face 12a of the rotor 12.

Each electrode 26a, 26b comprises a respective metal film 28a, 28b and a plurality of substantially parallel metal tracks 30a, 30b, the tracks of one of the electrodes being interleaved between the tracks of the other electrode. Thus, each of the electrodes 26a and 26b is in the form of a comb.

The tracks 30a and 30b of the electrodes are distributed over the inside face 12a of the rotor 12 in such a manner as to cover the greatest possible surface area. The metal forming the films 28a and 28b and the tracks 30a and 30b may be copper, for example.

As shown in FIG. 2, the metal film 28a, 28b of each electrode 26a, 26b of the detector device may extend substantially along the longitudinal axis X-X of the turbomachine, and the metal tracks 30a, 30b may extend in a direction extending substantially transversely relative to said axis X-X.

Alternatively, the metal tracks 30a, 30b of each electrode 26a, 26b of the detector device could extend substantially along the longitudinal axis X-X, and the metal film 28a, 28b could extend in a direction that is substantially transverse relative to said axis X-X (FIG. 3).

A conductor wire coil 32 constituting a secondary magnetic circuit and secured to the rotor 12 is connected to the electrodes 26a and 26b of the detector device. The coil is wound on the inside face 12a of the rotor 12. This coil 32, which is excited by the magnetic field created by the coil 22 of the electricity generator of the turbomachine, serves to apply a voltage between the electrodes 26a, 26b.

Thus, the detector device has its own power supply. While the turbomachine is in operation, rotation of the rotor 12 causes the coil 32 of the detector device to rotate relative to the coil 22 of the electricity generator, which generator coil is stationary. This leads to induced current appearing in the conductor wire of the coil 32 which applies a voltage across the electrodes 26a, 26b via a rectifier 33.

In a variant power supply for the electrodes 26a, 26b of the detector device, which variant is not shown, it is possible to envisage installing one or more magnets constituting a primary magnetic circuit on the inside face 14a of the stator 14 facing the coil 32. Thus, while the turbomachine is in operation, rotation of the rotor 12 causes the coil 32 of the detector device to rotate relative to said magnets, which are themselves stationary, thereby causing an induced current to appear in the coil of the detector device.

The presence of one or more magnets 24 of the electricity generator on the outside face 12b of the rotor 12 has the effect of magnetically attracting the ferromagnetic particles 34 that are present in the oil inside the enclosure 20 against the inside face 12a of the rotor. Such particles 34 are the result of wear of the ball bearing 18 (in particular by flaking).

When these ferromagnetic particles 34 are attracted to the inside face 12a of the rotor 12, they are received between the tracks 30a, 30b of the electrodes 26a, 26b of the detector device, thus closing the circuit. An electrical signal is thus generated between the electrodes 26a and 26b.

In other words, the detector device operates like a switch: as soon as ferromagnetic particles 34 are received between the tracks 30a, 30b of the detector, then contact is closed and an electrical signal is generated.

A detector 36 connected to the electrodes 26a, 26b serves to detect and measure the intensity of the electrical signal generated between said electrodes. The intensity of the electrical signal as detected is a function of the density of ferromagnetic particles 34 in contact with the tracks 30a, 30b of the detector device, i.e. with the density of particles that are present in the oil enclosure 20.

Figure 4:
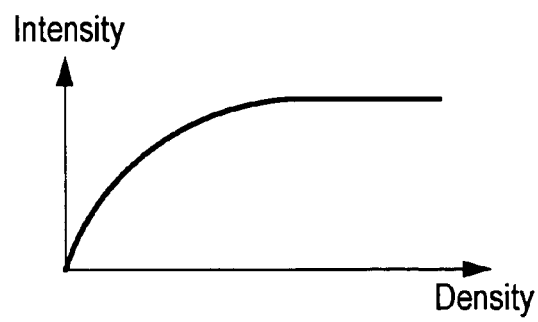
FIG. 4 is a graph plotting the intensity of the signal measured by the detector device as a function of the density of the collected ferromagnetic particles.

FIG. 4 plots a curve representing variation in the intensity of the detected electrical signal (up the ordinate) as a function of the density of ferromagnetic particles in contact with the tracks of the detector device (along the abscissa). From this curve, it can clearly be seen that the intensity of the electrical signal increases with increasing particle density until it reaches a ceiling.

According to an advantageous characteristic of the invention, the detector device further comprises a radio transmitter 38 connected to the detector 36. The transmitter 38 can transmit a radio signal to a FADEC electronic computer, which radio signal is a function of the density of ferromagnetic particles 34 present in the oil enclosure 20.

Thus, the FADEC is continuously informed in real time about the density of ferromagnetic particles 34 present in the oil enclosure 20, and thus about the wear state of the ball bearing 18 (where a high density of particles corresponds to a high degree of wear of the bearing balls).

As a result, it is no longer necessary to wait for the turbomachine to be subjected to maintenance on the ground in order to become aware of the wear state of the inter-shaft ball bearing. For example, in the event of ball bearing wear reaching a critical threshold, the FADEC can inform the pilot of the airplane that it is necessary to perform maintenance thereon next time the airplane is stopped.

What is claimed is:

1. A turbomachine having a longitudinal axis, the turbomachine comprising an annular rotor centered on the longitudinal axis of the turbomachine, an annular stator disposed coaxially around the rotor, at least one ball bearing disposed on the rotor and rotatably supporting said stator, the inside of the rotor defining part of an oil enclosure for cooling and lubricating the balls of the bearing, and an electricity generator having a secondary magnetic circuit secured to the stator and a primary magnetic circuit constrained to rotate with the rotor, the turbomachine further including a detector device for automatically detecting ferromagnetic particles in the oil enclosure, said detector device being powered electrically by electromagnetic induction, wherein the detector device comprises;

a pair of electrodes disposed on the inside annular face of the rotor; and a secondary magnetic circuit secured to the rotor, said circuit being excited by the magnetic field created by the secondary magnetic circuit of the electricity generator of the turbomachine so as to apply a voltage between the electrodes.

2. A turbomachine according to claim 1, wherein each electrode comprising a metal film and a plurality of substantially parallel metal tracks, each of the electrodes being interleaved with between the tracks of the other electrode; wherein when ferromagnetic particles are received between the tracks of the electrodes, an electrical signal is generated between said electrodes; and wherein a detector further comprises a detector for detecting the intensity of the electrical signal generated between the electrodes, the intensity of said electrical signal being a function of the ferromagnetic particles present in the oil enclosure.

3. A turbomachine according to claim 2, wherein the detector device further includes a radio transmitter connected to the detector in order to transmit a radio signal to a full authority digital engine controller of the turbomachine, which signal is a function of the density of ferromagnetic particles present in the oil enclosure.

4. A turbomachine according to claim 2, wherein the secondary magnetic circuit of the detector device is constituted by a coil of conductor wire.

5. A turbomachine according to claim 1, wherein the metal film of each electrode of the detector device extends substantially along the longitudinal axis of the turbomachine, and the metal tracks of each electrode extend in a direction that is substantially transverse relative to said longitudinal axis of the turbomachine.

6. A turbomachine according to claim 2, wherein the metal tracks of each electrode of the detector device extends substantially along the longitudinal axis of the turbomachine, and the metal film of each electrode extends in a direction that is substantially transverse relative to said longitudinal axis of the turbomachine.

7. A turbomachine according to claim 1, wherein the secondary magnetic circuit of the electricity generator is constituted by a coil wound on an inner annular face of the stator, and the primary magnetic circuit of the electricity generator is constituted by at least one magnet disposed on an outer annular face of the rotor.

8. A turbomachine according to claim 7, wherein the coil and the magnet(s) of the electricity generator are isolated from the oil enclosure by annular sealing devices secured to the stator.

9. A turbomachine according to claim 1, wherein the rotor and the and the stator belong to the high-pressure body of the turbomachine.

* * * * *